United States Patent [19]

Manella

[11] 4,302,164
[45] Nov. 24, 1981

[54] PERISTALTIC PUMP WITH MEANS COMPRESSING ITS TUBE IN TWO DIRECTIONS

[75] Inventor: Paul Manella, Dübendorf, Switzerland

[73] Assignee: Doltron AG, Uster, Switzerland

[21] Appl. No.: 84,654

[22] Filed: Oct. 15, 1979

[30] Foreign Application Priority Data

Nov. 29, 1978 [CH] Switzerland ............... 12227/78

[51] Int. Cl.³ .................. F04B 43/12; F04B 45/08
[52] U.S. Cl. .................................................. 417/474
[58] Field of Search ............................. 417/474, 475

[56] References Cited

U.S. PATENT DOCUMENTS

| | | | |
|---|---|---|---|
| 2,877,714 | 3/1959 | Serg et al. .................. | 417/474 X |
| 3,083,647 | 4/1963 | Muller ........................ | 417/474 |
| 3,227,091 | 1/1966 | Isreeli et al. ............... | 417/475 |
| 3,229,266 | 2/1969 | Jones .......................... | 417/474 |
| 3,433,171 | 3/1969 | Corneil ...................... | 417/474 |

FOREIGN PATENT DOCUMENTS 2543300  2/1977  Fed. Rep. of Germany ...... 417/474

OTHER PUBLICATIONS

Albo, Positive Displacement Pump, IBM Technical Disclosure Bulletin, pp. 1034–1035, vol. 7, No. 11, Apr. 1965.

*Primary Examiner*—Richard E. Gluck
*Attorney, Agent, or Firm*—Haseltine and Lake

[57] ABSTRACT

A hose pump comprising a number of movable pressure elements composed of a first pressure device and a second pressure device. The first pressure device is constituted by an element which is movable to-and-fro with respect to a counter pressure surface and the second pressure device contains elements movable to-and-fro with respect to a hose. The pressure devices are arranged next to one another and are driven by a common drive, in order to rhythmically compress the hose within two neighboring regions. The drive comprises cam discs structured to correspond to the number of pressure elements, the apex of crown points of the cam discs being mutually offset with respect to one another, in order to rhythmically compress the hose which is placed in the hose pump, and thus, to convey the medium which is to be pumped.

4 Claims, 4 Drawing Figures

PERISTALTIC PUMP WITH MEANS COMPRESSING ITS TUBE IN TWO DIRECTIONS

BACKGROUND OF THE INVENTION

The present invention relates to the pumping art, and, more specifically, concerns a new and improved construction of hose pump containing movable pressure elements.

In the case of hose pumps, a hose is rhythmically compressed in sections for the purpose of conveying a fluid medium. To this end the hose pump is either equipped with one or a number of squeeze rolls, arranged at a rotatable body, and a hose arranged at a circular arcuate-shaped surface, or with a number of adjacently arranged punches which are moved to-and-fro by cams and a flat or planar counter element. Conveying of the fluid medium is accomplished either by the rotating squeeze rolls or by successive contact of the punches against the counter element, so that the hose is continuously pressed in a peristaltic movement.

Experience has shown that the hose of such type hose pumps are exposed to large loads and subjected to pronounced mechanical wear. This wear is attributable to the continuously identical deformation of the hose, i.e. the hose is always compressed together at the same region, and the additional tensional load of the hose by the rotating squeeze rolls, or by the additional loading by virtue of the edges of the punches.

SUMMARY OF THE INVENTION

Therefore, with the foregoing in mind, it is a primary object of the present invention to provide a new and improved construction of hose pump which is not afflicted with the aforementioned drawbacks and limitations of the prior art constructions.

Another and more specific object of the present invention aims at a new and improved design of hose pump which is structured such that there is minimized the wear of the hose of the hose pump.

Yet a further significant object of the present invention relates to a new and improved construction of hose pump which is relatively simple in design, extremely reliable in operation, and not readily subject to breakdown or malfunction, and requires a minimum of maintenance and servicing.

Now in order to implement these and still further objects of the invention, which will become more readily apparent as the description proceeds, the hose pump of the present development is manifested by the features that the hose is rhythmicaly compressed together in two directions which are situated transversely with respect to one another.

Some of the more notable advantages which are realized with the invention reside essentially in the fact that due to the transversely extending deformation of the hose in adjacently situated or juxtapositioned hose sections, the plastic deformation, arising due to a one-sided deformation of the hose, is extensively avoided. Consequently, it is beneficially possible to also use hoses having reduced strength, and the dilatation of the hose is accomplished by the fluid medium and no longer is dependent upon the strength of the hose and the wall thickness of the hose.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE PREFERRED EMBODIMENTS

Figure 1:
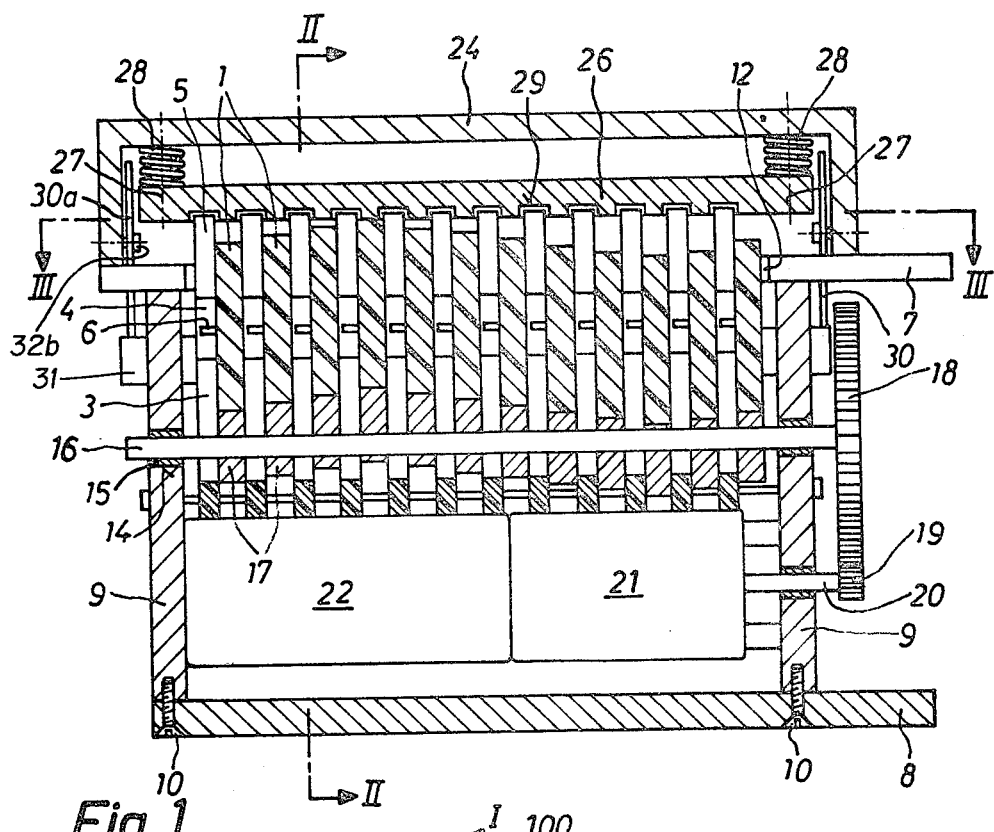
FIG. 1 is a longitudinal sectional view through a first exemplary embodiment of a hose pump constructed according to the invention.
Figure 2:
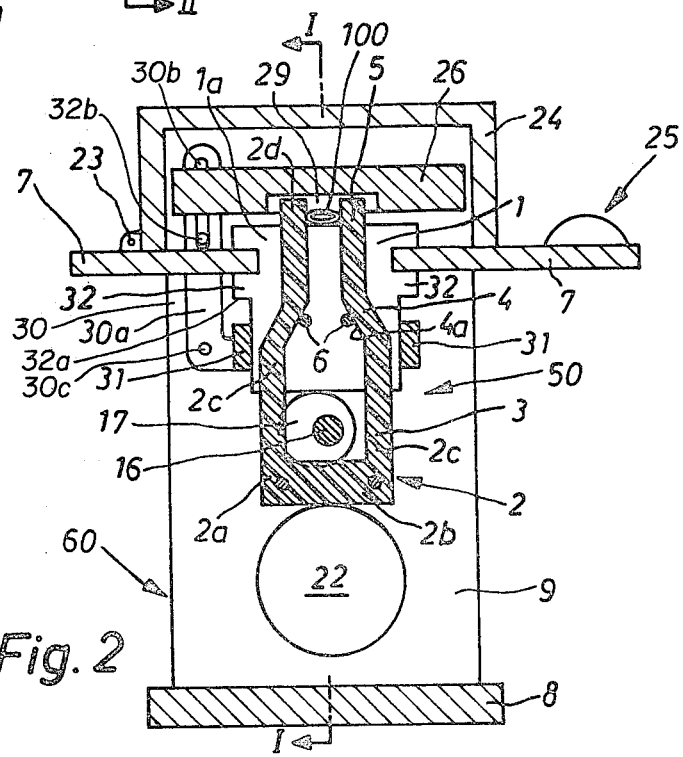
FIG. 2 is a sectional view of the hose pump of FIG. 1, taken substantially along the line II—II thereof.
Figure 3:
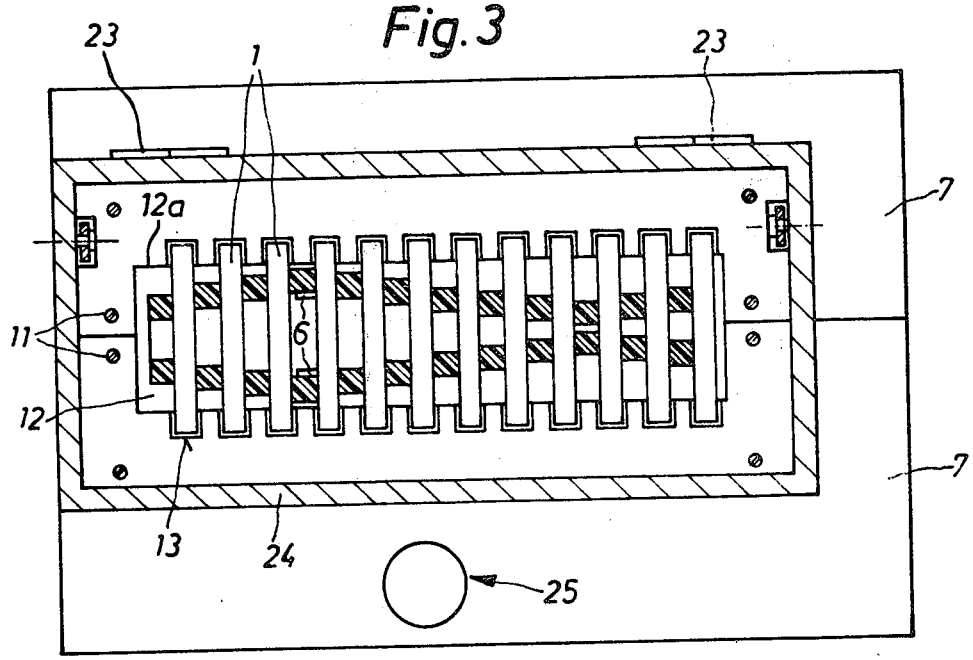
FIG. 3 is a top plan view of the hose pump of FIG. 1 wherein the cover has been omitted for purposes of revealing internal structure.

Describing now the drawings, it is to be understood that the exemplary embodiment of hose pump shown in FIGS. 1 to 3 is constructed as an insertable unit and can be inserted into a not particularly illustrated pump housing. In particular, it will be seen that the hose pump comprises twelve pressure elements, generally indicated by reference character 50, and which are arranged in a row. Each pressure element 50 comprises a first pressure device 1 and a second pressure device 2 which are arranged in mutual contact with one another. The first pressure device 1 is structured as a substantially rectangular plate 1a. The second pressure device 2 is constructed as a fork-shaped or bifurcated element 2a and bears against one side of the neighboring first pressure device 1. The second pressure device 2 contains a yoke or crossbar 2b and two legs 2c each of which contain an inclined intermediate portion or section 4. The free ends 2d of the legs 2c are constructed as essentially parallel almost closely situated portions or sections 5.

At the first pressure device 1 there are arranged pins 6 or equivalent structure in spaced relationship from one another. These pins 6 protrude from the pressure device 1 and bear against the inner surfaces 4a of the related intermediate portion or section 4 of the contacting second pressure device 2.

Continuing, it will be seen that the hose pump comprises a frame, generally indicated by reference character 60, composed of a substantially rectangular base plate 8, two upright plates 9, fixedly interconnected with one another by screws 10 or equivalent fastening devices, and a front plate 7 fastened opposite to the base plate 8 at the upright or vertical plates 9 by means of screws 11 or equivalent fastening devices. The front plate 7 has an elongate or lengthwise extending slot or recess 12 at each of the longitudinal sides 12a of which there are provided twelve cutouts or notches 13 arranged at the same spacing from one another and serving as guide means for the first pressure device 1.

In each of the plates or plate members 9 there is provided a respective bore or opening 14 in which there is pressed or otherwise appropriately mounted a respective bearing bushing or sleeve 15. Within these bearing means 15 there is rotatably mounted a drive shaft 16 upon which there are secured twelve cam discs 17. These cam discs 17 are arranged in spaced relationship with respect to one another, so that their circumferential surface bears in each case at one of the first pressure elements 1. The cam discs 17 are attached at the drive shaft 16 in such a manner that their apex points or crowns are offset with regard to one another, looking in the clockwise direction, by 30° in each case.

At one end of the drive shaft 16 there is attached a gear 18 which meshes with a pinion 19. This pinion 19 is secured to a power take-off shaft 20 of gearing or transmission means 21. The gearing 21 is secured to one of the upright plates 9 and is coupled with a drive motor 22.

Hinges 23 serve to pivotably mount a cover 24 at the front plate 7. Furthermore, a lock unit 25 for the cover or cover member 24 is provided at the front plate 7.

The cover 24 constitutes an elongate, substantially hood-shaped part in which there is arranged an elongate counter pressure plate 26. This counter pressure plate 26 is retained by pins 27 which are attached at the cover 24. Between the cover 24 and the counter pressure plate or surface 26 there are pressure or compression springs 28 which are retained by the pins 27. Hence, the counter pressure plate 26 is elastically retained. Recesses 29 are provided in the counter pressure plate 26, and when the cover 24 is closed, there protrude and are guided at such recesses 29 the free ends 2d of the second pressure device 2.

Fixedly connected with the cover 24 is a lifting device 30, so that upon opening the cover 24 all of the first pressure devices 1 are raised. The lifting device 30 comprises two bars 31 arranged transversely with respect to the pressure elements 1 and 2, such that each of these bars 31 can be brought into contact with the first pressure member 1. The first pressure member 1 is a substantially rectangular plate provided with projections 32, each forming a shoulder 32a. The lifting device 30 comprises 2 rod means 30a connected to said bars 31 at one end and connected with the cover 24 at the other end. Each rod means 30a is provided with a slot 30b and is movably mounted on the cover 24 by means of a pin 32b received within the slot 30b. During the opening of the cover 24 the rod means 30a is being moved. Thus the bars 31 are lifted and brought into contact with shoulders 32c and lift pressure members 1 to uppermost level when said cover is opened completely. By lifting said pressure members 1 the corresponding pressure members 2 are spread by pin 6 fixed on said pressure members 1. When the cover is opened completely, said pressure members 1 are on their uppermost level and said pressure members 2 are spread most widely such that a hose can be inserted directly. FIGS. 1 and 2 show that each rod means 30a consist of two levers pivotally connected to each other by pin 30c. One of said levers is fixed to the bars 31 and the other lever is pivotably mounted to the cover 24. Conversion of the swing of the pin 32b into the linear motion of the bars is caused by said pin 30c.

Having now had the benefit of the description of the hose pump, there will be described its mode of operation, particularly based upon the showing of FIG. 4.

Figure 4:
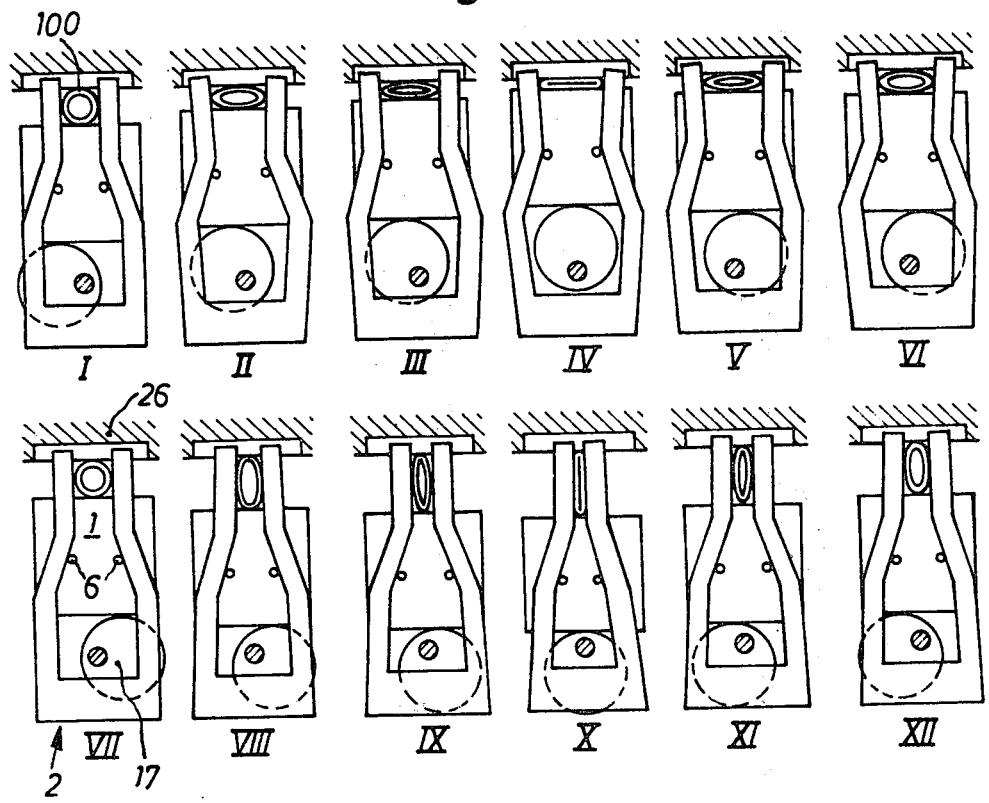
FIG. 4 is a schematic illustration of the position of the pressure elements with respect to one another.

In FIG. 4 there have been illustrated twelve positions of the pressure elements during one revolution of the cam disc 17, and the starting position has been randomly chosen. In the starting position, designated by reference character I, the hose 100 is in a state where it possesses its complete cross-sectional area. By means of the cam disc which rotates in clockwise direction, the first pressure device 1 is displaced in the direction of the counter pressure surface. Hence, the cross-sectional area of the hose is continuously reduced. Due to displacement of the first pressure device the free ends of the legs of the second pressure device 2 are continuously spread by the pins 6 which bear at the intermediate portions of the legs. In the position IV the hose 100 has been completely compressed together. Due to the elastic legs, during the further rotation of the cam disc in a clockwise direction, the first pressure device is displaced away from the counter pressure plate or surface 26. This displacement is caused by the spring force of the legs 2c, which downwardly press the first pressure device 1 by means of the pins 6 bearing at the intermediate sections 4. At the same time, the hose 100 is continuously deformed by the free ends 2d of the legs, in a direction located transversely with respect to the counter pressure plate or surface 26, so that the hose 100 continuously reaches its complete cross sectional area (position VII) and then is completely compressed together (position X). Thereafter, the first pressure device 1 is again displaced in the direction of the counter pressure plate or surface 26 and the free ends 2d of the legs 2c are spread, so that the hose 100 again assumes its complete cross-sectional area. Then there is again initiated the previously described operation.

Yet, FIG. 4 also shows the positions of the twelve pressure elements relative to one another and which are arranged in the hose pump.

The quantity of fluid medium which is conveyed by the hose pump is governed by the rotational speed of the drive means. Any suitable control can be used for this purpose, which need not be here further considered since it does not constitute subject matter of the present invention and is unimportant for understanding the underlying concepts and principles thereof.

While there are shown and described present preferred embodiments of the invention, it is to be distinctly understood that the invention is not limited thereto, but may be otherwise variously embodied and practiced within the scope of the following claims. Accordingly,

What is claimed is:

1. A hose pump for conveying a fluid medium through a hose comprising a plurality of movable pressure elements consisting of a first set of pressure members and a second set of pressure members, a common drive means for activating said first and second sets of pressure members in order to progressively change the cross-sectional are of the hose along its length successively in two directions situated transversely with respect to one another, and means defining a counter pressure surface and said first pressure members are movable to-and-fro with respect to the counter pressure surface, wherein: each first pressure member is a plate of substantially rectangular shape, two pins are provided at a side of each said plate which bear against an adjacent second pressure member, each said second pressure member comprising a bifurcated part having a yoke and two legs, the free end portions of which define two elements movable to-and-fro with respect to the hose, each of the legs having an intermediate portion directed towards one another and said pins being against inner surfaces of said intermediate portions in order to continuously alter the spacing between free end of said legs.

2. The hose pump as defined in claim 1, further including: two guide elements provided for the first pressure member; said common drive means comprising a drive shaft; cam disc means secured to said drive shaft, in order to displace each first pressure member against the counter pressure surface; and said hose being insertable between the counter pressure surface and said first pressure member.

3. The hose pump as defined in claim 1, wherein: each second pressure member is formed of an elastic material; the free ends of each said leg members being structured to possess portions which extend essentially parallel to one another and almost are situated next to one another and between which the hose is insertable.

4. The hose pump as defined in claim 1, further including frame means in which there are arranged said pressure elements and said drive means, a cover, hinging means for pivotable mounting said cover at said frame means; wherein said cover has an inner surface, a lifting device comprising two bars arranged transversely with respect to said first pressure members and two rod means, each connected with said cover and each connected to said bars such that all of said first pressure members are raised upon opening said cover.

* * * * *